US005424067A

United States Patent [19]

Brancq et al.

[11] Patent Number: 5,424,067

[45] Date of Patent: * Jun. 13, 1995

[54] INJECTABLE MULTI-PHASE EMULSIONS

[75] Inventors: Bernard Brancq, Le Chesnay; Gérard Trouve, Castres, both of France

[73] Assignee: Societe d'Exploitation de Produits pour les Industries Chimiques (S.E.P.P.I.C.), Paris, France

[*] Notice: The portion of the term of this patent subsequent to Jun. 6, 2012 has been disclaimed.

[21] Appl. No.: 778,843

[22] PCT Filed: Jun. 29, 1990

[86] PCT No.: PCT/FR90/00484

§ 371 Date: Feb. 28, 1992

§ 102(e) Date: Feb. 28, 1992

[87] PCT Pub. No.: WO91/00106

PCT Pub. Date: Jan. 10, 1991

[30] Foreign Application Priority Data

Jul. 3, 1989 [FR] France ................................ 89 08917

[51] Int. Cl.[6] ...................... A61K 39/39; A61K 9/113

[52] U.S. Cl. .............................. 424/184.1; 424/278.1; 514/785

[58] Field of Search .................... 424/88, 184.1, 278.1; 514/785

[56] References Cited

U.S. PATENT DOCUMENTS

| | | |
|---|---|---|
| 3,983,228 | 9/1976 | Woodhour et al. . |
| 4,069,313 | 1/1978 | Woodhour et al. . |
| 4,795,635 | 1/1989 | Peleg et al. . |
| 4,803,070 | 2/1989 | Cantrell et al. . |

OTHER PUBLICATIONS

Al-Dabbass et al., "Immunizing Activity of Oil Adjuvant Attenuated Spore Vaccine of *Bacillus anthracis* in Sheep, " *J. Vet. Med.* B 33, 340-345 (1986).

Woodard, L., "Adjuvant Activity of Water-Insoluble Surfactants," *Lab. Animal Sci.*, vol. 39, No. 3, pp. 222-225 (1989).

Yamamoto et al (1978) Abstract only, Jpn J Med Sci Biol 31(3): 263-276.

Yamamoto et al (1978) Abstract only, Jpn J Med Sci Biol 31(5-6): 393-406.

Barteling (1980) Abstract Only Tijdschr Diergeneeskd 105(17): 695-698.

Francis et al (1983) Abstract Only JH7G 91(2): 329-334.

Michalek et al (1983) Abstract Only Mol Immunol 20(9): 1009-1118.

*Primary Examiner*—Christine M. Nucker

*Assistant Examiner*—Nita M. Minnifield

*Attorney, Agent, or Firm*—Poms, Smith, Lande & Rose

[57] ABSTRACT

The present invention relates to injectable multi-phase solutions of W/O/W type, usable as vaccines or as vehicles of active substances in human and veterinary medicine, which are pharmaceutically acceptable in each one of their constituents, stable for at least 12 months in storage at 4° C., of viscosity less than 300 mPas and comprise at least the following constituents:

an oily adjuvant composed of:

a water-immiscible oily phase representing between 20 and 70% of the formula, an emulsifying system selected so that the inversion point of the resulting emulsion ranges between 25° and 45° and represents between 2 and 10% of the formula, an aqueous phase containing the antigens or the active substances and representing between 20 and 78% of the formula and obtained in a single mixing operation.

8 Claims, No Drawings

INJECTABLE MULTI-PHASE EMULSIONS

The present invention relates to multi-phase emulsions usable for administering active substances or antigens by injectable route; such emulsions constitute new well tolerated vehicles permitting a gradual release of the active substances or antigens.

The invention finds a particular application in multi-phase vaccines, in the immunity adjuvants contained therein, and in their preparation processes.

Immunity adjuvants are products which increase the reactions of the immunity system when they are administered in the presence of antigens of virus, bacterial or synthetic origin: they cause a massive appearance of macrophages on the injection site, in the lymphatic nodules, they increase the production of specific immunoglobulins (antibodies) and stimulate a great number of cells implied in the immunity defense mechanisms.

Among these adjuvants, it is recognized that those resulting from the association of a mineral oil with a mannitol ester, optionally containing a dead mycobarterium and known under the name of Freund's adjuvants (FIA) are the most efficient.

Vaccines produced by mixing equal quantities of Freund's adjuvant and antigenic medium remain a reference throughout the world for immunological research in laboratories. These vaccines are in the form of emulsions with continuous oily phase (W/O), which are very viscous (about 5000 mPas at 20° C.), hence difficult to inject and moreover with poor stability: dephasing is observed after a few days.

Said vaccines are very badly tolerated and cause in animals, at the injection site, very serious local reactions with oedemae, abscesses and necroses, which are unacceptable to the Public Health authorities and which render cattle meat unfit for consumption.

In humans, anti-diphtheric vaccines produced with the Freund's complete adjuvant have caused severe intolerances, and in some cases even abortions.

To improve the injectability of such vaccines, a method consisting in re-dispersing them in an aqueous phase containing a hydrophilic surface-active agent (Polysorbate 80) has been described by HERBERT (The LANCET 16, 771, 1965).

The resulting double emulsions are fluid, but their stability only lasts a few days.

The hydrophilic surface-active agent used is toxic towards the cells since it is known to be widely used in biology for eliminating lipids from cellular membranes.

The preparation of this type of multiple emulsions is delicate: it is dependent not only on the composition of the phases but also on the operational method used: authors, using the ultrasonic stirring method described by HERBERT, have obtained a multiple emulsion by sonication for 10 secs, whereas the same formula is of W/O type if sonication is continued for 30 secs.

Such great variability in the parameters of the method which, moreover, requires two steps, is not readily acceptable at the industrial level.

From an immunity standpoint, the vaccines obtained with this method have proved less efficient than the W/O type vaccines. (ANDERSON. Res. Vet. Sci 12, 18, (1971) HERBERT. Immunological standardization. Symposium series 6, 29, (1967)).

It would therefore be advantageous to obtain emulsions that are fluid, readily injectable, stable and of W/O/W type at room temperature and which could be transformed, at the temperature of the human or animal body into a more efficient W/O type preparation.

Such transformation, called phase inversion, has been studied at great length by SHINODA and his team. The temperature at which form W/O passes to form W/O/W is the phase inversion temperature. It is determined by following the electric conductivity of an emulsion produced under heat and cooled in an ice bath.

The phase inversion occurs with a lot of non-ionic surface-active agents although it has been mainly studied with products of ethoxylated alkyl phenol type, which are incompatible with medical or veterinary applications.

The emulsions object of the present invention are produced in one operation, from pharmaceutically acceptable emulsifyiers which, when dissolved in an injectable oil, form a homogeneous clear phase and have inversion points approaching the temperatures of the human or animal bodies. It has also been observed, quite unexpectedly, that said vaccines are very well tolerated and do not cause any local reactions, abscesses or necroses as do the W/O type vaccines produced from the same oil.

Characterization of the emulsion according to the invention.

The emulsions obtained are characterized by the following properties:

fluidity: the viscosities, measured with a BROOKFIELD apparatus at 20° C., are always below 300 mPs and generally below 100 mPas;

injectability: the emulsions flow easily out of a 10 ml syringe equipped with a needle of 0.8 mm diameter and subjected to a constant pressure of 3.3 kg.

The time required for 10 ml of emulsion to flow out is comparable to that required for an O/W formula and considerably shorter than that required for an emulsion containing Freund's adjuvant.

| Emulsion | Flowing time (s) |
| --- | --- |
| According to the invention | |
| (W/O/W) | 9 |
| O/W | 6.5 |
| containing FIA | |
| (W/H) | 59 | conductivity: this determines the nature of the continuous phase of the emulsion. It can generally vary between 0.1 and 10 mS in cold conditions and between 0.05 and 5 mS in hot conditions.

dispersibility in water: the emulsions obtained according .to the invention are readily dispersable in water with which they form a milky solution with an oily film.

aspect under the microscope: the emulsions according to the invention have oil drops sizes below or close to 1 μm.

The microdrops of aqueous solution in said oil drops are invisible under an optical microscope. The sizes of said particles, which are rather small in comparison with the sizes of the HERBERT type formulae, explain the good stability of the vaccines according to the invention:

stability: the emulsions according to the invention are stable for at least 12 months at 4° C.

In order to determine whether it has been possible to produce a multiple emulsion from a mixture of oil, emulsifier and antigenic medium under stirring, according to the operational method of the invention, it is sufficient to place a few drops of the resulting preparation in a container of water and to stir gently with a spatula.

A water-in-oil type emulsion gives separate white drops which will rapidly gather up together and float on the surface of the water.

An oil-in-water type emulsion gives a milk of homogeneous color and appearance.

A multiple emulsion gives both a homogeneous milk and droplets floating on the water surface.

Characterization of the oils contained in injectable emulsions.

The oils must be non-toxic and give fluid emulsions under storage at 4° C.

They are selected from mineral, vegetable or animal oils known for their low toxicity. The selected mineral oils will be straight chain mineral oils and contain more than 16 carbon atoms, they will also be free of aromatic compounds.

Known examples are the MARKOL 52 (produced by ESSO France) or the DRAKEOL 6VR (produced by PENRECO USA).

It is also possible to use synthetic hydrocarbons such as polyisobutene or polyisoprene.

Suitable vegetable oils will be oleic type unsaturated oils which are biodegradable and known for their immunogenic power, such as ground-nut oil, olive oil, sesame oil, soya bean oil, corn oil, jojoba oil, etc. . . .

Examples of suitable animal oils, to which the same criteria of tolerance and immunological efficiency apply, are squalene, squalane and spermaceti oil.

Fatty acid esters with at least 14 carbon and alcohol atoms, which are preferably branched and liquid at storage temperature can also be used.

For example, according to a particular characteristic of the invention, the oil used is a mineral oil or a synthetic hydrocarbon, liquid at 4° C. and having a viscosity lower than 100 mPas at 40° C.

According to another characteristic of the invention, the oil used is a metabolizable virgin or refined oil or liquid wax of vegetable nature.

According yet to another characteristic of the invention, the oil used is of animal origin, particularly fish oil.

The oil used according to the invention can also be a mixture of two or more of the above-described oils.

Characterization of the emulsifiers.

The emulsifiers are non-ionic products without any noticeable toxicity, usable by injectable route, which can be selected in the following chemical classes, given by way of example and non-restrictively:
  esters or ethers of fatty acids and sugar (SORBITOL, MANNITOL, SACCHAROSE, GLUCOSE, . . . ),
  esters of fatty acid and glycerol or polyol,
  hydrophilic derivatives of said esters obtained by grafting of alcohol, ether-oxide, carboxylic, amine, amide and other functions,
  lecithins
  fatty acids or alcohols condensed with ethylene and-/or propylene oxide.

The fatty chains of the emulsifiers used will have between 8 and 22 carbon atoms, and preferably between 14 and 20 carbon atoms. Liquid chains are preferred.

The alcohols and oleic, ricinoleic, linoleic, isostearic, cetostearic acids and their derivatives are choice compounds.

The emulsifiers of the mannitol oleates family are particularly advantageous on account of their innocuousness and of their ability to form very stable multi-phase emulsions. Mannitol oleate derivatives obtained by grafting hydrophilic functions such as for example, the amine, amide, ethoxy, alcohol, polyol, carboxylic and other functions, can advantageously be used.

Ready-to-use immunity adjuvants which contain oil and emulsifiers and which are in the form of a clear oily, stable and homogeneous liquid constitute the preferred embodiment of the emulsifiers used in the invention.

Method for obtaining W/O/W type multi-phase vaccines

It is important, in order to obtain very stable vaccines, to produce them as follows:
  bring both the oily phase (oil and emulsifiers), and the aqueous phase containing the antigens or the active substances, to the same temperature selected between 20 and 40° C. A temperature of 30° C. is often optimal,
  pour the aqueous phase into the oily phase under moderate non-splitting stirring and stir until the mixture is back to room temperature.

Formulations that are stable for over a year at 4° C. and at room temperature are obtained according to this process.

EXAMPLE 1

A vaccine is produced which has the following composition:

| | |
|---|---|
| Oily adjuvant | 50% |
| Bovine albumine buffer solution at 100 ug/ml | 50% |

The composition of the oily adjuvant is so selected that the inversion point of the emulsion is about 35° C.

The characteristics of this adjuvant and of the corresponding vaccine are given in Table 1—1.

This vaccine is injected subcutaneously to SWISS mice. The evolution of the antibody level (average monitored on 10 mice) determined by an ELISA technique is given in Table 1-2.

For comparison, said table also shows the evolutions of the antibody levels observed for a vaccine produced with Freund's incomplete adjuvant (FIA) or for an albumine buffer solution containing no immunity adjuvant.

The vaccine described in this example enables a significant and durable increase of the antibody level in mice, comparatively to a vaccine containing no adjuvant, without however reaching the performances of the vaccine containing FIA.

TABLE 1 - 1

PHYSICO-CHEMICAL CHARACTERISTICS OF THE BSA VACCINE

| Characteristics of the adjuvant | | |
|---|---|---|
| ASPECT | clear oil of straw yellow color | |
| COMPOSITION | fluid mineral oil | 86% |
| | oleic ester of anhydromannitol and of PEG * 500 | 14% |
| Acid index | 0.15 | |
| Hydroxyl index | 18 | |
| Saponification index | 15 | |
| Refraction index | 1.461 | |
| Viscosity | 25 mPas | |
| Characteristics of the vaccine (at 20° C.) | | |
| Type | E/H/E | |
| Particle size | <1 μm | |

TABLE 1 - 1-continued

PHYSICO-CHEMICAL CHARACTERISTICS OF THE BSA VACCINE

| | |
|---|---|
| Conductivity | 1.0 mS |
| Viscosity | 50 mPas |
| Stability 4° C. | >12 months |

* PEG : polyethyleneglycol

TABLE 1 - 2

ANTI BSA ANTIBODY LEVEL (EXPRESSED IN INVERSE RATIO OF THE DILUTION NECESSARY TO OBTAIN AN OPTICAL DENSITY EQUAL TO (1)

| | DAYS AFTER VACCINE ADMINISTRATION | | | |
|---|---|---|---|---|
| | 14 | 28 | 56 | 125 |
| VACCINE ACCORDING TO EXAMPLE 1 | 95 | 1295 | 2785 | 2225 |
| VACCINE ON IFA | 475 | 7560 | 17280 | 25600 |
| ALBUMINE WITHOUT ADJUVANT | 60 | 157 | 102 | 105 |

The antigenic material is constituted of an Influenza A/PR8 virus inactivated with formol titrating 800 haemagglutinating units/ml.

Adjuvant and vaccine have substantially the same physico-chemical characteristics as those in Example 1. The vaccine inversion point is 37°C.

Vaccination is conducted in a single injection of 0.2 ml by subcutaneous route.

Table 2 gives the results of a dosing of antibodies (expressed in log2 of the dilutions). It is found that the multi-phase vaccine is as efficient as the corresponding vaccine on FIA and definitely more efficient than the control vaccine containing no adjuvant.

EXAMPLE 2

A vaccine against influenza is tested in SWISS mice. It has the following composition:

| | |
|---|---|
| oily adjuvant (mineral oil containing oleic esters of PEG 500 and anhydromannitol) | 47% |
| antigenic material | 53% |

TABLE 2

PERFORMANCE OF A MULTI-PHASE INFLUENZA VACCINE

| VACCINE | ANTIBODY LEVEL 42 days after vaccination |
|---|---|
| multiphase | 4.3 |
| containing FIA | 4.9 |
| containing no adjuvant | 3.1 |

EXAMPLE 3

Two vaccines against AUJESZKY's disease were prepared from the same antigenic material. One is a conventional oily vaccine of W/O type (3A), the other being a multi-phase W/O/W vaccine according to the invention (3B).

The adjuvants contained in these two vaccines are based on a liquid synthetic oil, obtained by polymerizing isobutylene. The multi-phase vaccine contains an emulsifying system which confers to it an inversion point of about 33° C.

The characteristics of the vaccines and of their adjuvants are given in Table 3-1.

TABLE 3 - 1

| FORMULA | 3A | % | 3B | % |
|---|---|---|---|---|
| CHARACTERISTICS OF ADJUVANT | | | | |
| Aspect | clear, pale yellow | | clear, pale yellow | |
| Oil | polyisobutene | 88% | polyisobutene | 85% |
| Emulsifier | mannitol monooleate | 12% | mannitol monooleate | 7.5% |
| | | | PEG 10 oleate | 7.5% |
| Acid index | 0.12 | | 0.15 | |
| Viscosity | 50 mPas | | 60 mPas | |
| CHARACTERISTICS OF VACCINE AT 20° C. | | | | |
| Viscosity | 100 mPas | | 88 mPas | |
| Droplet size | 1 to 5 μm | | 1 μm | |
| Conductivity | 0.15 uS | | 3.9 mS | |
| Type | W/O | | W/O/W | |
| Stability 4° C. | >12 months | | >12 months | |

Two batches of six pigs bred for pork-butchery in a pig's rearing farm were vaccinated. Vaccination was carried out by intramuscular injection of 2 ml of vaccine, followed by a booster injection 15 days later. The antibody levels were estimated by seroneutralization 59 days after the first injection.

Table 3-2 clearly shows the advantage of the multi-phase vaccine 3B which causes only very slight intolerance reactions (necrosis, suppuration, fibrosis, muscular atrophy), while giving a positive immunological response as proved by the setology results and by the presence of macrophagic granulomae.

TABLE 3 - 2

| VACCINATION RESULTS | | |
|---|---|---|
| VACCINE | 3A | 3B |
| SEROLOGY (hemagglutination) | | |
| Antibody level (10 g2) | 2.6 | 1.3 |
| HISTOLOGY* | | |
| necrosis | 1/6 | 0/6 |
| suppuration | 3/6 | 0/6 |
| fibrosis | 6/6 | 3/6 |
| serious muscular atrophy | 2/6 | 1/6 |
| macrophagic granulomae | 4/6 | 6/6 |

*Frequency of the lesions observed

EXAMPLE 4

This experiment also emphasizes the good tolerance of a multi-phase vaccine according to the invention comparatively to a conventional W/O type oily vaccine prepared with the same mineral oil.

The characteristics of the two oily adjuvants and of the two vaccines thus obtained are given in Table 4-1.

Two batches of pigs bred for pork butchery in a pig rearing farm were vaccinated against AUJESZKY's disease.

2 ml of vaccine were administered to each animal by intramuscular route; a booster injection was administered in the same way 18 days after the first injection. A resistance test was conducted 32 days after the vaccination by intranasal spraying of 4 ml of an infectious virus solution. Table 4-2 sums up the results.

The weight evolution of the two groups of animals after the experiment, are comparable and definitely higher than that of the control animals vaccinated without adjuvant, The antibody level (expressed as inverse dilution ratio) are not significantly different.

On the contrary, the tolerance of the multi-phase vaccine 4B is considerably improved: no necrotic abscesses or local reaction, unacceptable to the health authorities, were noted.

This is coupled to moderate rises in temperatures noted with this vaccine during the 2 vaccinations.

TABLE 4 - 1
CHARACTERISTICS OF THE VACCINES AGAINST AUJESKY'S DISEASE

| FORMULA | 4A | % | 4B | % |
|---|---|---|---|---|
| CHARACTERISTICS OF ADJUVANT | | | | |
| Oil | Fluid mineral oil | 89% | Fluid mineral oil | 85% |
| Emulsifier | Oleic acid and mannitol ester | 11% | Mannitol and of PEG 500 oleic ester | 15% |
| Hydroxyl index | 12 | | | |
| Acid index | 0.11 | | 0.2 | |
| Saponification index | 14 | | 17 | |
| Refraction index (25° C.) | 1.459 | | 1.460 | |
| Viscosity (20° C.) | 40 mPas | | 20 mPas | |
| CHARACTERISTICS OF THE VACCINE | | | | |
| Type | W/O | | W/O/W | |
| Viscosity (20° C.) | 25 mPas | | 112 mPas | |
| Microscopic aspect | drops about 1 μm | | drops 1 μm | |
| Conductivity (20° C.) | 0.28 μS | | 1.3 mS | |
| Stability at 4° C. | >12 months | | >12 months | |
| Antigen titre | 10 9 DCP 50/ml | | 10 9 DCP 50/ml | |

TABLE 4 - 2
RESULTS OF VACCINATION OF PIGS

| VACCINE | 4A | 4B |
|---|---|---|
| HYPERTHERMIA | | |
| at the time of vaccination | + | − |
| at the time of the booster | +++ | + |
| at test time | + | ++ |
| MEAN WEIGHT EVOLUTION | | |
| (for the 7 days following test NB. Vaccine without adjuvant - 1.08 | +0.17 | +0.15 |
| SEROLOGY | | |
| Antibody build-up rate | 22.4 | 13.6 |
| type difference | 8.8 | 11.2 |
| LOCAL REACTIONS | | |
| Abcess - necrosis | 4/4 | 0/5 |
| Suppuration | 1/4 | 0/5 |
| Fibrosis | 3/4 | 2/5 |
| Muscular atrophy | 3/4 | 5/5 |
| Macrophagic granulomae | 3/4 | 2/5 |

TABLE 5

| FORMULA | 32 A | % | 3408 | % | 26 K | % |
|---|---|---|---|---|---|---|
| CHARACTERISTICS OF THE ADJUVANT | | | | | | |
| Oil | Mineral and fluid | 85% | squalane | 85% | mineral and fluid oleic ester | 88% |
| Emulsifier | lecithin | 7.8% | Mannitol and PEG 400 oleic ester | | Mannitol and PEG 400 | |
| | PEG monooleate | 7.2% | | 15% | clear, pale yellow | 12% |
| Aspect | clear yellow | | clear, pale yellow | | | |
| Viscosity 20° C. | 35 mPas | | | | 30 mPas | |
| CHARACTERISTICS OF THE VACCINE | | | | | | |
| Type | multi-phase | | multi-phase | | multi-phase | |
| % adjuvant | 50 | | 50 | | 70 | |
| Viscosity | 30 mPas | | 100 mPas | | 150 mPas | |
| Conductivity | 3 mS | | 2 mS | | 1.8 mS | |
| Aspect under the microscope (droplet size) | <1 μm | | 1 μm | | 1 μm | |

| FORMULA | GTAF 56 | % | V 7401 - 1 | % | V7401 - 2 | % |
|---|---|---|---|---|---|---|
| CHARACTERISTICS OF THE ADJUVANT | | | | | | |
| Oil | Ground-nut oil | 92% | mineral oil + ground-nut oil (1:1) | 84% | mineral oil + ground-nut oil (1:1) | 87% |
| Emulsifier | copolymer OE/OP | 8% | oleic acid and mannitol ester | 16% | mannitol and oleic acid ester + | 13% |

TABLE 5-continued

| Aspect | pale yellow | clear, pale yellow | lecithin clear, yellow |
|---|---|---|---|
| Viscosity | 50 mPas | 45 mPas | 50 mPas |
| CHARACTERISTICS OF THE VACCINE | | | |
| Type | multi-phase | multi-phase | multi-phase |
| % additive | 65 | 64 | 60 |
| Viscosity | 1800 mPas | 450 mPas | 100 mPas |
| Conductivity | 1.9 mS | 2 mS | 2 mS |
| Microscopic aspect (droplet size) | 1 μm | 1 μm | 1 μm |

EXAMPLE 5

This example describes placebo emulsions and corresponding adjuvants (Table 5), all of which have the following characteristics:
- poor viscosity
- good injectability
- inversion around 30°–40° C.
- correct stability in storage at 4° C.

These examples show that it is possible to produce vaccines according to the invention from different oils usable by injectable route (mineral, vegetable, squalane, and such oils), and mixtures thereof, as well as different types of emulsifiers provided that their concentration is adapted. The quantity of aqueous phase containing the active substances can also vary to a large extent.

It has nonetheless been noted that the characteristics of the resulting emulsions, and in particular the viscosity, stability and inversion point, are very sensitive to the composition of the adjuvants and to the origin of the oils used.

EXAMPLE 6

A tolerance test to intraperitoneal injection of 0.25 ml of product has been described by S. S. BERLIN (Annals of Allergy 20, 473 (1962)). The vaccines according to the invention have gone successfully through all the norms of this test (no death, no peritonitis, no weight evolution as in the controls).

Test according to the protocols described in the European Pharmacopeia have shown that there was no abnormal toxicity in the placebo vaccines according to the invention, in particular those prepared from oleic esters of mannitol and of PEG, and from fluid mineral oil or polyisobutylene synthetic oil.

EXAMPLE 7

This example illustrates the importance of the preparation process on the physico-chemical properties of multi-phase vaccines, and in particular the preparation temperature.

The formulae under study have the following composition:

| | |
|---|---|
| oily adjuvant (mineral oil 85%, oleic esters of mannitol and PEG 15%) | 94 g |
| Placebo antigen material | 106 g |

Operational Method 1—The two phases are brought to 30° C. and stirred together for 10 mins. in an YS-TRAL agitator turning at about 2500 rev/min.

Operational Method 2—The oily phase is heated to 40° C., the aqueous phase is kept to room temperature.

Aspect of the resulting vaccines as observed under the microscopes:

| Operational Method 1 | Operational Method 2 |
|---|---|
| Very fine droplets (<1 μm) and homogeneous | Droplets able to reach up to 50 μm - heterogeneous |

We claim:

1. A parental vaccine preparation in the form of a multi-phase W/O/W emulsion which comprises on a weight basis:
   20 to 78% of an aqueous phase containing one or more antigens;
   20 to 70% of a water immiscible oily phase comprising one or more oils selected from the groups consisting of: mineral oils or synthetic hydrocarbons which are liquid at 4° C. and have a viscosity lower than 100 mPas at 40° C.; synthetic oils having at least 14 carbon atoms; metabolizable oils or waxes of vegetable origin or virgin refined oils; and oils or waxes of animal origin;
   2 to 10% of an emulsifying system comprising one or more non-ionic and non-toxic emulsifiers selected from the group consisting of: esters of fatty acids and of sorbitol; esters of fatty acids and of sorbitol condensed with ethylene oxide or propylene oxide; esters of fatty acids and of mannitol; esters of fatty acids and of mannitol condensed with ethylene oxide or propylene oxide; esters of fatty acids and of mannitol grafted with hydrophilic groups selected from the group consisting of carboxylic acid, amine, amide, alcohol, polyol, ether, oxide; esters of fatty acids and of anhydromannitol; esters of fatty acids and of anhydromannitol grafted with hydrophilic groups selected from the group consisting of carboxylic acid, amine, amide, alcohol, polyol, ether, oxide; esters of fatty acids and of saccharose; esters of fatty acids and of saccharose condensed with ethylene oxide or propylene oxide; esters of fatty acids and of glycerol; esters of fatty acids and polyol; esters of fatty acids and of glycerol condensed with ethylene oxide or propylene oxide; fatty acids condensed with ethylene oxide or propylene oxide; fatty alcohols condensed with ethylene oxide or propylene oxide; and glycerophospholipid so that the inversion point of the resulting emulsion ranges between 25° C. and 45° C.; and
   said preparation being pharmaceutically acceptable in each one of its constituents and stable for 12 months in storage at 4° C. and having a viscosity at 20° C. less than 300 mPas.

2. A preparation according to claim 1, wherein said fatty acids have been 12 and 22 carbon atoms.

3. A preparation according to claim 2, wherein said fatty acids are selected from the group consisting of oleic acid, stearic acid and ricinoleic acid.

4. A preparation according to claim 1, wherein said emulsifying system comprising at least one emulsifier selected from the group consisting of:
- mannitol oleate;
- mannitol oleate grafted with hydrophilic group selected from carboxylic acid, amine, amide, alcohol, polyol, ether, oxide;
- anhydromannitol oleate;
- anhydromannitol oleate grafted with hydrophilic groups selected from carboxylic acid, amine, amide, alcohol, polyol, ether, oxide.

5. A preparation according to claim 1, wherein said oily phase comprises one or more oils selected from the group consisting of:
- mineral oils having a straight chain containing more than 16 carbon atoms and being free of aromatic compounds;
- synthetic hydrocarbons selected from polysobutene and polylsoprene;
- unsaturated and biodegradable vegetable oils;
- animal oils selected from squalene, squalane and spermaceti oil;
- esters of fatty acids and alcohol having at least 14 carbon atoms.

6. A parenteral vaccine preparation in the form of a multi-phase W/O/W emulsion which comprises on a weight basis;
- 20 to 78% of an aqueous phase containing one or more antigens;
- 20 to 70% of a water immiscible oily phase comprising one or more oils selected from the group consisting of:
  mineral oils or synthetic hydrocarbons which are liquid at 4° C. and have a viscosity lower than 100 mPas at 40° C.; synthetic oils having at least 14 carbon atoms; metabolizable oils or waxes of vegetable origin or virgin or refined oils; and oils or waxes of animal origin;
- 2 to 10% of an emulsifying system comprising one or more non-ionic and non-toxic emulsifiers selected from the group consisting of: fatty acids condensed with ethylene oxide or propylene oxide; oleic esters of mannitol; oleic esters of mannitol grafted with hydrophilic groups selected from the group consisting of carboxylic acid, amine, amide, alcohol, polyol, ether, oxide; oleic esters of anhydromannitol; oleic esters of anhydromannitol grafted with hydrophilic groups selected from the group consisting of carboxylic acid, amine, amide, alcohol, polyol, ether, oxide so that the inversion point of the resulting emulsion ranges between 25° C. and 45° C.; and
- said preparation being pharmaceutically acceptable in each one of its constituents and stable for 12 months in storage at 4° C. and having a viscosity at 20° C. less than 300 mPas.

7. A preparation according to claim 6, wherein said fatty acids are selected from the group consisting of oleic acid, stearic acid and ricinoleic acid.

8. A preparation according to claim 6, wherein said synthetic hydrocarbons are selected from the group consisting of polyisobutene and polyisoprene and said animal oils are selected from the group consisting of squalene, squalane and spermaceti oil.

* * * * *